(12) United States Patent
Brower, III et al.

(10) Patent No.: US 11,414,448 B2
(45) Date of Patent: Aug. 16, 2022

(54) METHOD FOR THE ENRICHMENT OF REBAUDIOSIDE B AND/OR REBAUDIOSIDE D IN STEVIA-DERIVED GLYCOSIDE COMPOSITIONS USING ADSORB-DESORB CHROMATOGRAPHY WITH A MACROPOROUS NEUTRAL ADSORBENT RESIN

(71) Applicant: CARGILL, INCORPORATED, Wayzata, MN (US)

(72) Inventors: Robert Joshua Brower, III, Englewood, OH (US); Ting Liu Carlson, Marietta, SC (US); Aron Broman Erickson, Albertville, MN (US); Jenna Helgeson, Otsego, MN (US); Andrew Keith Ohmes, Jordan, MN (US); Troy Allen Rhonemus, Plymouth, MN (US); Christopher Austin Tyler, Minnetonka, MN (US); Tougeu Vang, Minnetonka, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 16/724,864

(22) Filed: Dec. 23, 2019

(65) Prior Publication Data
US 2020/0140473 A1 May 7, 2020

Related U.S. Application Data

(60) Division of application No. 15/649,194, filed on Jul. 13, 2017, now abandoned, which is a continuation of application No. 13/885,113, filed as application No. PCT/US2011/061386 on Nov. 18, 2011, now abandoned.

(60) Provisional application No. 61/415,548, filed on Nov. 19, 2010.

(51) Int. Cl.
| | |
|---|---|
| *C07H 1/06* | (2006.01) |
| *C07H 1/08* | (2006.01) |
| *C07H 15/24* | (2006.01) |
| *C07H 15/256* | (2006.01) |
| *A23L 27/30* | (2016.01) |

(52) U.S. Cl.
CPC ............ *C07H 1/06* (2013.01); *C07H 1/08* (2013.01); *C07H 15/24* (2013.01); *C07H 15/256* (2013.01)

(58) Field of Classification Search
CPC ....... A23L 27/36; A23L 27/30; C07H 15/256; C07H 1/06; C07H 1/08
See application file for complete search history.

(56) References Cited

U.S. PATENT DOCUMENTS

| | | | |
|---|---|---|---|
| 4,361,697 A | 11/1982 | Dobberstein | |
| 4,599,403 A | 7/1986 | Kumar | |
| 4,997,659 A | 3/1991 | Yatka | |
| 5,061,320 A | 10/1991 | Goodacre | |
| 5,204,115 A | 4/1993 | Olinger | |
| 5,496,487 A | 3/1996 | Capeci | |
| 5,962,678 A * | 10/1999 | Payzant | ........... A23L 27/36 536/127 |
| 5,972,120 A | 10/1999 | Kutowy | |
| 6,124,442 A | 9/2000 | Zhou | |
| 6,180,157 B1 | 1/2001 | Fotos | |
| 6,228,996 B1 * | 5/2001 | Zhou | ........... C07G 3/00 536/128 |
| 6,365,217 B2 | 4/2002 | Fotos | |
| 7,582,154 B2 | 9/2009 | Propst | |
| 7,838,044 B2 | 11/2010 | Abelyan | |
| 9,024,012 B2 | 5/2015 | Erickson | |
| 2002/0001652 A1 | 1/2002 | Dron | |
| 2003/0026872 A1 | 2/2003 | Dake | |
| 2003/0170310 A1 | 9/2003 | Wadhwa | |
| 2005/0226983 A1 | 10/2005 | Bakal | |
| 2006/0083838 A1 * | 4/2006 | Jackson | ........... A61P 3/10 426/548 |
| 2006/0134292 A1 | 6/2006 | Abelyan | |
| 2007/0059419 A1 | 3/2007 | Catani | |
| 2007/0082103 A1 | 4/2007 | Magomet | |
| 2007/0116800 A1 | 5/2007 | Prakash | |
| 2007/0116829 A1 | 5/2007 | Prakash | |
| 2007/0292582 A1 | 12/2007 | Prakash | |
| 2008/0107775 A1 | 5/2008 | Prakash | |
| 2008/0292764 A1 | 11/2008 | Prakash | |
| 2008/0292775 A1 | 11/2008 | Prakash | |
| 2008/0300402 A1 | 12/2008 | Yang | |
| 2009/0017185 A1 | 1/2009 | Catani | |
| 2009/0162500 A1 | 6/2009 | Mui | |
| 2009/0312293 A1 | 12/2009 | Mazzola | |
| 2010/0099857 A1 | 4/2010 | Evans | |
| 2010/0137569 A1 | 6/2010 | Prakash | |

(Continued)

FOREIGN PATENT DOCUMENTS

| | | |
|---|---|---|
| CN | 101090642 A | 12/2007 |
| CN | 101220062 A | 7/2008 |
| CN | 101270138 A | 9/2008 |
| CN | 101366496 A | 2/2009 |
| CN | 101472487 A | 7/2009 |
| CN | 102060892 A | 5/2011 |
| CN | 102093447 A | 6/2011 |
| EP | 334617 A2 | 9/1989 |
| JP | 5123300 B1 | 7/1976 |

(Continued)

*Primary Examiner* — Ryan B Huang

(57) ABSTRACT

The invention relates to the use of adsorb/desorb chromatography to prepare enriched compositions comprising rebaudioside B and/or rebaudioside D. Compositions with enriched rebaudioside-B and/or rebaudioside-D components may be prepared from *Stevia*-derived glycoside compositions using an adsorb-desorb chromatography process where the stationary phase of the chromatography bed comprises a macroporous neutral adsorbent resin.

6 Claims, 9 Drawing Sheets

(56) References Cited

U.S. PATENT DOCUMENTS

2011/0087011 A1* 4/2011 Chiang .................... C07H 1/08
  536/18.1

FOREIGN PATENT DOCUMENTS

| | | | |
|---|---|---|---|
| JP | 58212759 | A | 12/1983 |
| JP | 01206969 | A | 8/1989 |
| WO | 1998011878 | A1 | 3/1998 |
| WO | 2000049036 | A1 | 8/2000 |
| WO | 2001060842 | A2 | 8/2001 |
| WO | 2006038221 | A1 | 4/2006 |
| WO | 2006045023 | A2 | 4/2006 |
| WO | 2006072879 | A1 | 7/2006 |
| WO | 2007149672 | A2 | 12/2007 |
| WO | 2008030121 | A1 | 3/2008 |
| WO | 2008091547 | A2 | 7/2008 |
| WO | 2008147723 | A1 | 12/2008 |
| WO | 2009006208 | A2 | 1/2009 |
| WO | 2009137838 | A1 | 11/2009 |
| WO | 2009140394 | A1 | 11/2009 |
| WO | 2010118218 | A1 | 10/2010 |
| WO | WO-2011112892 | A1 * | 9/2011 ............... C07H 1/06 |
| WO | 2012088598 | A1 | 7/2012 |
| WO | WO-2012088598 | A1 * | 7/2012 ........... A23L 1/2215 |
| WO | 2012108894 | A1 | 8/2012 |
| WO | 2012166163 | A1 | 12/2012 |

* cited by examiner

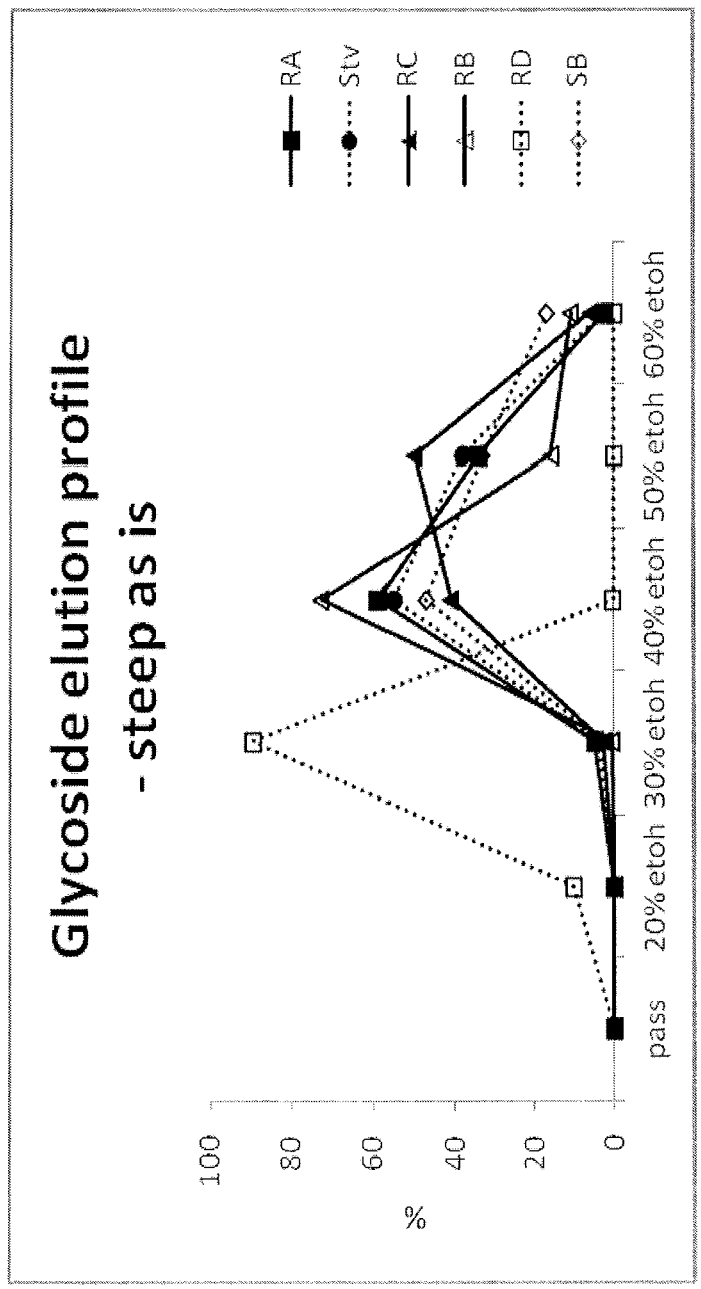
Figure 2: Recovery of various glycosides in steepwater after treatment with SP710 at a pH of 5.8.

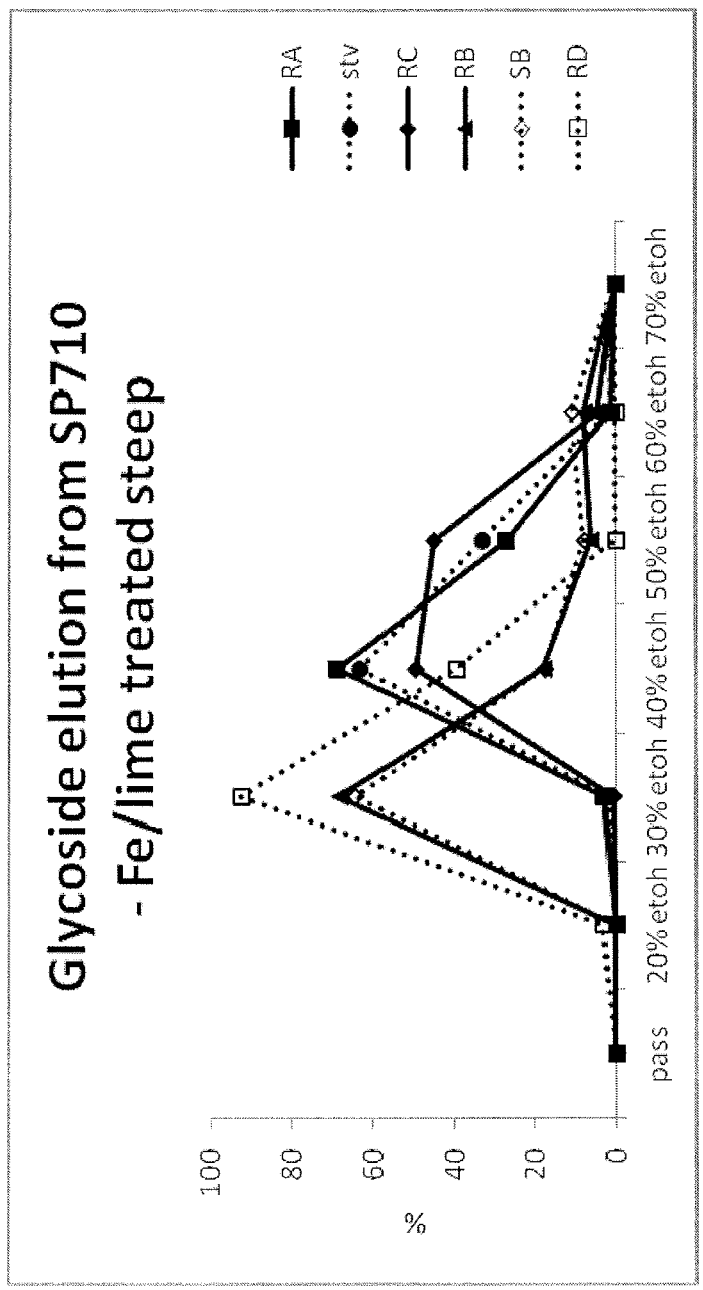
Figure 3: Recovery of various glycosides in of steepwater, treated with Ferric Chloride and Lime, after treatment with SP710.

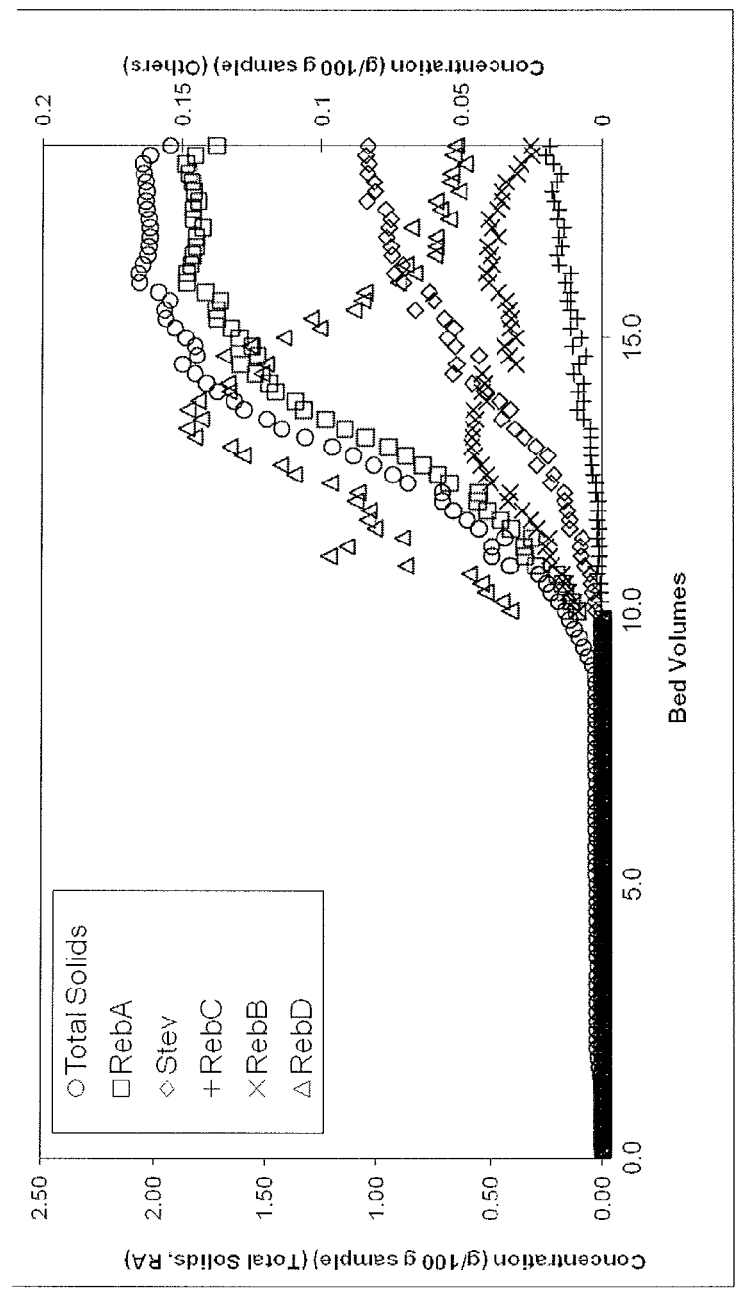
Figure 4: Concentration of glycosides eluted from SP70 during loading with steepwater.

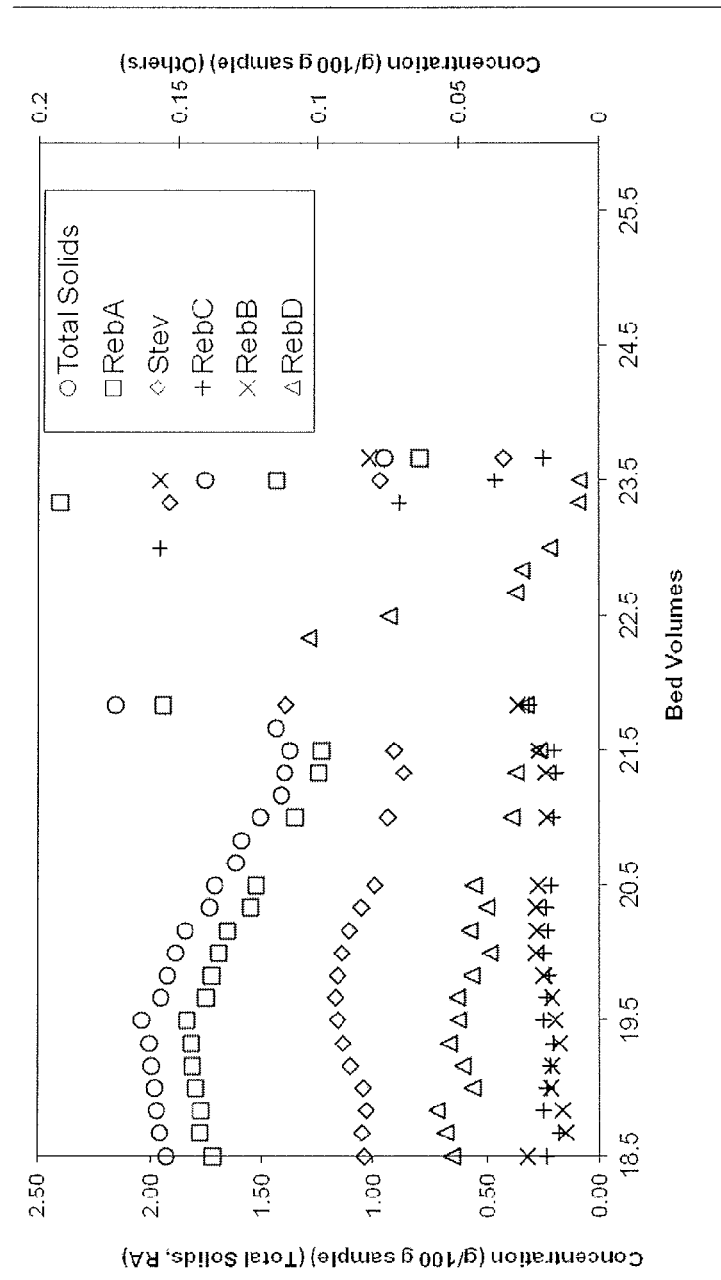
Figure 5: Concentration of glycosides eluted from SP70 during wash with 15% ethanol and elution with 100% ethanol.

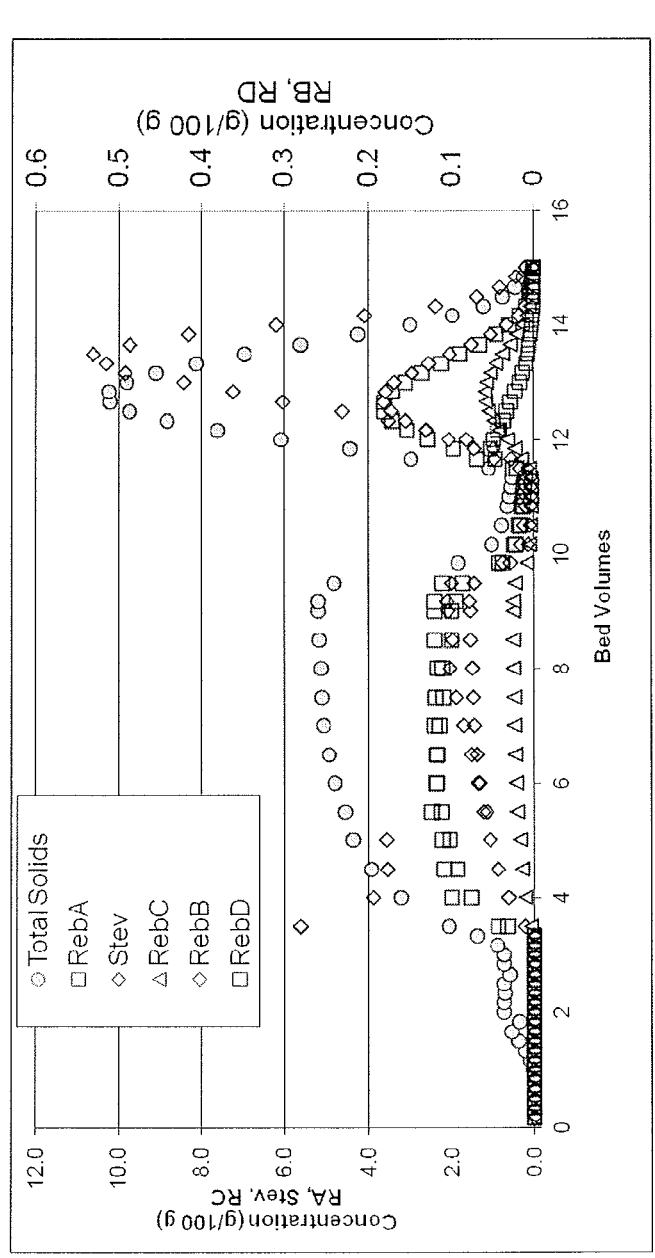
Figure 6: Concentration of glycosides during loading, wash, and eluting of SP70 at pH 2.

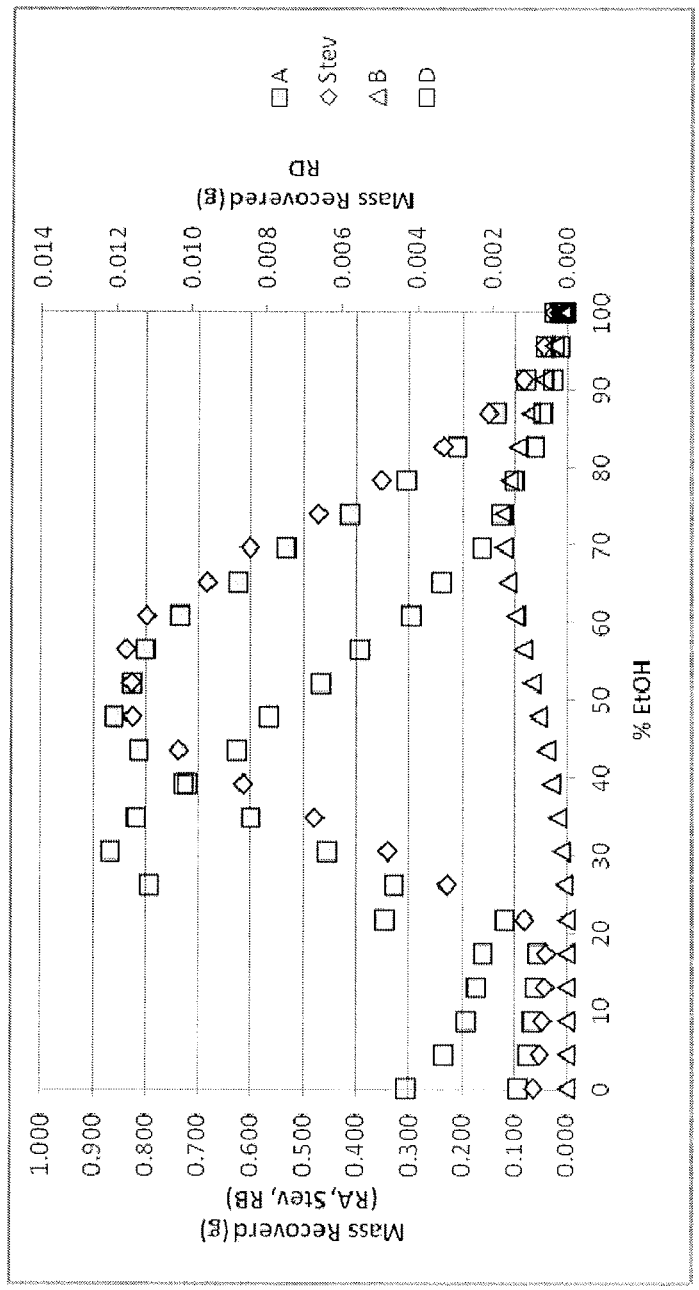
Figure 7: Recovered of glycosides during eluting of SP70 at pH 2 versus the ethanol concentration of the eluent.

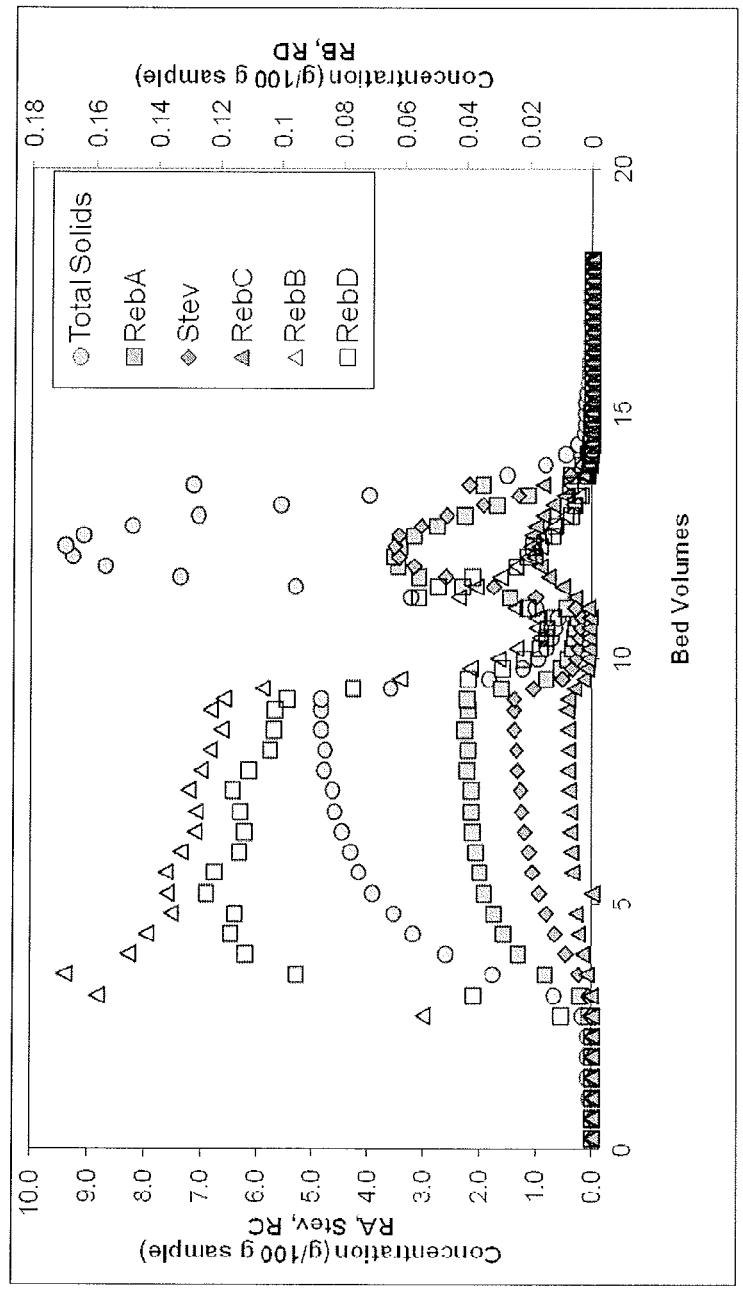
Figure 8: Concentration of glycosides during loading, washing, and eluting.

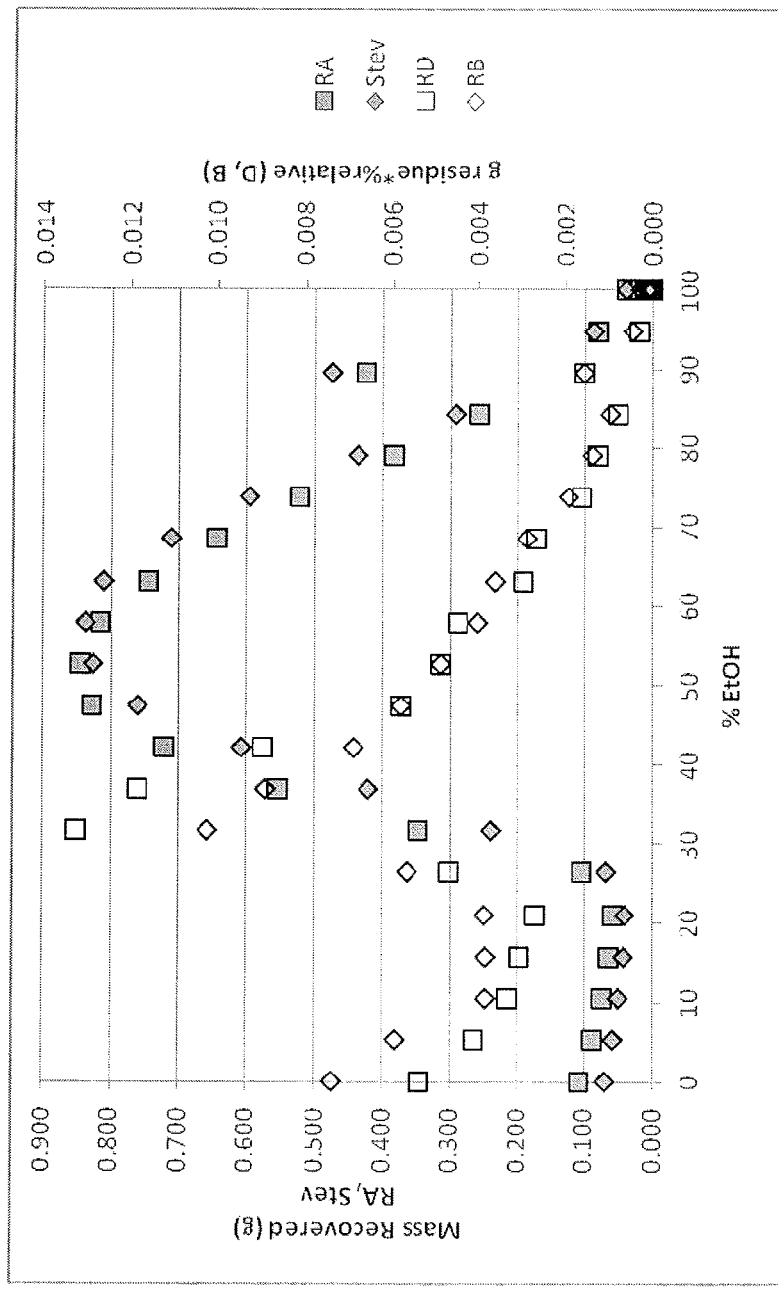
Figure 9: Mass of RA, Stev, RB and RD collected during elution.

METHOD FOR THE ENRICHMENT OF REBAUDIOSIDE B AND/OR REBAUDIOSIDE D IN STEVIA-DERIVED GLYCOSIDE COMPOSITIONS USING ADSORB-DESORB CHROMATOGRAPHY WITH A MACROPOROUS NEUTRAL ADSORBENT RESIN

CROSS REFERENCE TO RELATED APPLICATION

This application is a divisional application of U.S. patent application Ser. No. 15/649,194, filed Jul. 13, 2017, entitled METHOD FOR THE ENRICHMENT OF REBAUDIOSIDE B AND/OR REBAUDIOSIDE D IN *STEVIA*-DERIVED GLYCOSIDE COMPOSITIONS USING ADSORB-DESORB CHROMATOGRAPHY WITH A MACROPOROUS NEUTRAL ADSORBENT RESIN which is a continuation application of U.S. patent application Ser. No. 13/885,113, filed May 13, 2013, entitled METHOD FOR THE ENRICHMENT OF REBAUDIOSIDE B AND/OR REBAUDIOSIDE D IN *STEVIA*-DERIVED GLYCOSIDE COMPOSITIONS USING ADSORB-DESORB CHROMATOGRAPHY WITH A MACROPOROUS NEUTRAL ADSORBENT RESIN, which is a national phase application of PCT/US2011/061386, filed Nov. 18, 2011, entitled METHOD FOR THE ENRICHMENT OF REBAUDIOSIDE B AND/OR REBAUDIOSIDE D IN *STEVIA*-DERIVED GLYCOSIDE COMPOSITIONS USING ADSORB-DESORB CHROMATOGRAPHY WITH A MACROPOROUS NEUTRAL ADSORBENT RESIN, which in turn claims the benefit of U.S. Provisional Patent Application 61/415,548, filed Nov. 19, 2010, entitled METHOD FOR THE ENRICHMENT OF REBAUDIOSIDE B AND/OR REBAUDIOSIDE D IN *STEVIA*-DERIVED GLYCOSIDE COMPOSITIONS USING ADSORB-DESORB CHROMATOGRAPHY WITH A MACROPOROUS NEUTRAL ADSORBENT RESIN, each of which is hereby incorporated by reference in its entirety.

FIELD OF THE INVENTION

The invention relates to the use of adsorb/desorb chromatography to prepare enriched compositions comprising rebaudioside B and/or rebaudioside D (reb-B and/or reb-D). As described herein, it has been discovered that enriched reb-B and/or reb-D can be prepared from *Stevia*-derived glycoside compositions using an adsorb-desorb chromatography process where the stationary phase of the chromatography bed comprises a macroporous neutral adsorbent resin. Examples of useful resins include "SP70" and "SP710" (from Mitsubishi) and "FPX66" (from Dow).

SUMMARY OF THE INVENTION

In some embodiments, the invention provides a method of preparing an enriched composition comprising at least one of reb-B, reb-D, or a mixture thereof, the method comprising the steps of:
(A) providing a pH adjusted *Stevia*-derived glycoside solution comprising: (i) at least one glycoside selected from the group of reb-B and reb-D; (ii) at least one other *Stevia*-derived glycoside;
(B) providing a macroporous neutral adsorbent resin;
(C) contacting the macroporous neutral adsorbent resin with the *Stevia*-derived glycoside solution so that at least a portion of glycosides in the *Stevia*-derived glycosides solution are adsorbed onto the adsorbent;
(D) providing at least one elution solvent comprising an ethanol and water mixture formulated to selectively elute reb-B, reb-D, or a mixture thereof from the adsorbent;
(E) contacting the macroporous neutral adsorbent resin with the ethanol and water elution solvent in order to elute a composition enriched with at least one glycoside selected from the group of reb-B and reb-D; and
(F) optionally, eluting at least a portion of the remaining adsorbed glycosides from the macroporous neutral adsorbent resin.

In certain embodiments of the present invention, the pH of the *Stevia*-derived glycoside solution can be an alkaline pH. In some of these embodiments, the pH of the pH adjusted *Stevia*-derived glycoside solution can range from a pH of about 8 to a pH of about 11. In other embodiments, pH of the pH adjusted *Stevia*-derived glycoside solution can range from a pH of about 8 to a pH of about 10. In some of these embodiments, the at least one elution solvent comprises from about 20-35% w/w ethanol and from about 65-80% w/w water. In other embodiments, the at least one elution solvent comprises from about 25-33% w/w ethanol and from about 67-75% w/w water. In these embodiments, the composition enriched with at least one glycoside is enriched with reb-B and reb-D. In some of these embodiments, at least a portion of the remaining adsorbed glycosides are eluted from the macroporous neutral adsorbent resin with a subsequent elution solvent wherein the subsequent elution solvent comprises from about 36-100% w/w ethanol and about 0-64% w/w water, and the composition eluted with the subsequent elution solvent is enriched with reb-A.

In other particular embodiments of the present invention, the pH of the *Stevia*-derived glycoside solution can be a slightly acidic pH. In these embodiments, the pH of the pH adjusted *Stevia*-derived glycoside solution can range from a pH of about 4 to a pH of about 7. In some of these embodiments, the at least one elution solvent comprises from about 20-35% w/w ethanol and from about 65-80% w/w water. In other embodiments, the at least one elution solvent comprises from about 25-33% w/w ethanol and from about 67-75% w/w water. In these embodiments, the composition enriched with at least one glycoside is enriched with reb-D. In some of these embodiments, at least a portion of the remaining adsorbed glycosides are eluted from the macroporous neutral adsorbent resin with a subsequent elution solvent wherein the subsequent elution solvent comprises from about 36-100% w/w ethanol and about 0-64% w/w water, and the composition eluted with the subsequent elution solvent is enriched with reb-A and reb-B.

In yet other particular aspects of the present invention, the pH of the *Stevia*-derived glycoside solution can be a very acidic pH. In these embodiments, the pH of the pH adjusted *Stevia*-derived glycoside solution can range from a pH of about 1 to a pH of about 4. In other embodiments, the pH of the pH adjusted *Stevia*-derived glycoside solution can range from a pH of about 1 to a pH of about 3. In some of these embodiments, the at least one elution solvent comprises from about 40-65% w/w ethanol and from about 35-60% w/w water. In other embodiments, the at least one elution solvent comprises from about 40-60% w/w ethanol and from about 40-60% w/w water. In these embodiments, the composition enriched with at least one glycoside is enriched with reb-A and reb-D. In some of these embodiments, at least a portion of the remaining adsorbed glycosides are eluted from the macroporous neutral adsorbent resin with a subsequent elution solvent wherein the subsequent elution solvent comprises from about 61-100% w/w ethanol and about 0-39% w/w water, and the composition eluted with the subsequent elution solvent is enriched with reb-B.

In embodiments of the present invention, the macroporous neutral adsorbent resin comprises a macroporous resin of divinyl benzene. The present invention is also directed to enriched compositions prepared according to the methods described herein.

BRIEF DESCRIPTION OF THE DRAWINGS

FIG. 2 is a graph of the recovery of various glycosides for each elution of Example 1.

FIG. 3 is a graph of the glycoside profile of the samples eluted at different ethanol concentrations in Example 2.

FIG. 4 is a graph of the concentration of glycosides eluting from the column during loading in Example 3.

FIG. 5 is a graph of the concentration of glycosides eluting from the column during a wash with 15% ethanol and elution with 100% ethanol in Example 3.

FIG. 6 is a graph of the concentration of glycosides during loading, washing, and eluting in Example 4.

FIG. 7 illustrates the mass of rebaudioside A, stevioside, rebaudioside B, and rebaudioside D collected during elution in Example 4.

FIG. 8 is a graph of the concentration of glycosides during loading, washing, and eluting in Example 5.

FIG. 9 illustrates the mass of rebaudioside A, stevioside, rebaudioside B, and rebaudioside D collected during elution in Example 5.

DETAILED DESCRIPTION

Figure 1A:
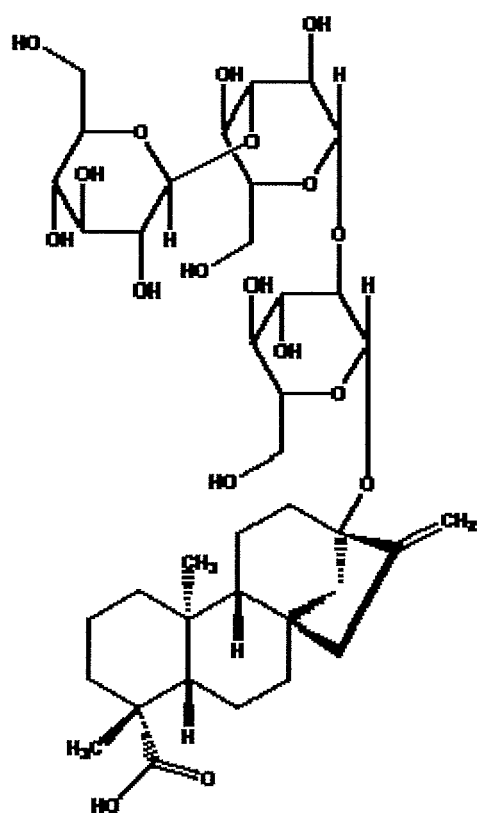
FIGS. 1A and 1B illustrate the structures of "rebaudioside B" and "rebaudioside D."
Figure 1B:
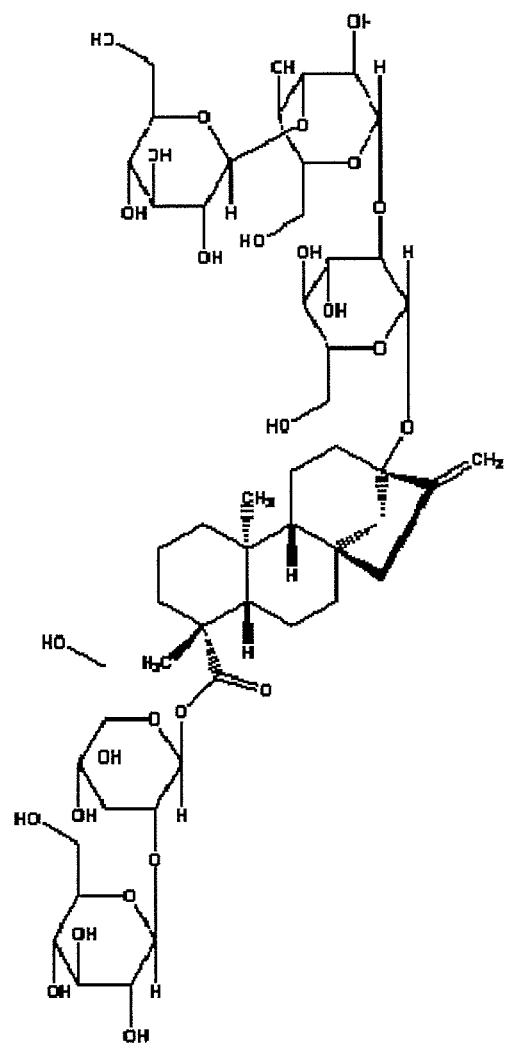

Reb-B and reb-D have desirable sensory properties. For example, reb-B is less bitter than reb-A and has slightly less sweetness. Pure component sensory data indicate a reduction in bitterness in reb-B, indicating that blends of reb-B and reb-A may have less bitterness. Reb-D has similar or more intense sweetness as compared to reb-A with substantially reduced bitterness. It is anticipated that blends of reb-D, reb-B and reb-A will have improved taste because of the reduced bitterness of reb-D and reb-B.

The present invention provides for methods of enriching reb-B and/or reb-D in order to utilize the desirable properties in sweetener compositions.

The method of the invention may also be used to create enriched compositions comprising reb-A by using the process to remove at least a portion of the reb-B and/or reb-D from a composition comprising reb-A.

In the method of the invention, the *Stevia*-derived glycoside solution may be a solution prepared from *Stevia* leaf extract, or the *Stevia*-derived glycoside solution may be the mother liquor of a crystallization process. In some embodiments, the *Stevia*-derived glycoside solution may be the product of the enrichment process of the invention when multiple enrichment steps are desired. Examples of glycosides that may be present in the *Stevia*-derived glycoside solution include reb-A, reb-B, reb-C, reb-D, reb-F, stevioside, dulcoside-A, steviolbioside, and rubusoside.

In some embodiments, the *Stevia*-derived glycoside solution that is used as a starting material in the method of the invention comprises steep water produced by steeping *Stevia* leaf in water at a ratio of about 10:1 water to leaf to about 100:1 water to leaf, more typically about 20:1 to about 50:1.

The steeping is typically conducted for about 1 to about 24 hours, more typically about 2 hours. The steep water typically contains about 0.1 to about 5.0 wt % solids, more typically about 1 to about 2 wt % solids. Steep water may also be produced by multiple extractions of the leaf in counter-current or co-current extraction to improve the recovery of steviol glycosides.

The solids present in the steep water typically range from about 15 to about 30 wt % glycosides, more typically about 20 wt % to about 25 wt % glycosides. The glycosides present vary depending on the variety of *Stevia* leaf. Typically, reb-A and stevioside comprise about 50% to about 80% of the glycosides present, with a ratio of reb-A to stevioside of about 4:1 to about 1:4, more typically about 2:1 to about 1:2.

In some embodiments, the *Stevia*-derived glycoside solution can be concentrated prior to adsorption. The solution can be concentrated to 10-50 wt % solids, more typically 20-40%. (g solids/100 g solution)

In some embodiments, the *Stevia*-derived glycoside solution that is used as a starting material in the method of the invention comprises a major amount of reb-A, and one or more impurities selected from reb-B and reb-D. Typically, the total amount of both reb-B and reb-D in the impure reb-A composition can vary up to about 6 wt %. For example, in some embodiments the impure reb-A composition comprises about 90 wt % to about 96 wt % reb-A; about 1 wt % to 4 wt % reb-B; and about 1 wt % to about 4 wt % reb-D.

In some embodiments, the *Stevia*-derived glycoside solution used as a starting material in the method of the invention comprises a partially purified extract from the *Stevia* leaf comprising about 10 wt % to about 90 wt % reb-A; about 0 wt % to about 40 wt % stevioside; about 0 wt % to about 5 wt % reb-B; and about 0 wt % to about 5 wt % reb-D. In other embodiments, the *Stevia*-derived glycoside solution comprises about 80 wt % steviol glycosides; about 40% to about 80 wt % reb-A; about 20 to about 40 wt % stevioside; about 1 to about 5 wt % reb-B, and about 1 to about 5 wt % reb-D.

In many embodiments, the *Stevia*-derived glycoside solution comprises a solvent. Solvent compositions for the *Stevia*-derived glycoside solution typically comprise water or a mixture of a lower alcohol (e.g., a $C_1$-$C_3$ alcohol) and water. Examples of lower alcohols include methanol, ethanol, and propanol (e.g., n-propanol and i-propanol). Mixtures of two or more alcohols and water may also be used. In many embodiments the solvent composition comprises water only. In other embodiments, the solvent comprises about 5 wt % to about 30 wt % lower alcohol and about 95 wt % to about 70 wt % water, based on the total weight of the solvent composition. More typically, the solvent composition comprises about 5 wt % to about 20 wt % lower alcohol and about 95 wt % to about 80 wt % water.

The *Stevia*-derived glycoside solution typically comprises about 1 wt % to about 20 wt % dissolved solids and about 99 wt % to about 80 wt % solvent. In some embodiments, the *Stevia*-derived glycoside solution comprises about 2 wt % to about 5 wt % dissolved solids and about 98 wt % to about 95 wt % solvent.

In the method of the invention, the stationary phase adsorbent comprises a macroporous neutral adsorbent resin. Useful stationary phase adsorbents include macroporous resins of divinyl benzene, such as those commercially available under the trade designations "SEPABEADS® SP70", "SEPABEADS® SP710", "SEPABEADS® SP825", "SEPABEADS® SP850", "DIAION™ HP20", and "DIAION™ HP21" (from Mitsubishi) and "AMBER- LITE™ FPX66" (from Dow). SP70 is reported to have a surface area of 800 m²/g, a pore radius of 70 Angstroms, and a mean particle diameter of 0.45 mm. FPX66 is described as a macroreticular aromatic polymer having a surface area of 700 m²/g, and a particle size of 0.6 to 0.75 mm.

In some embodiments, it is advantageous to adjust the pH of the *Stevia*-derived glycoside solution to a pH ranging from a pH of about 7 to a pH of about 11. In other embodiments, the pH of the *Stevia*-derived glycoside solution can be adjusted to a pH ranging from a pH of about 8 to a pH of about 11. In yet other embodiments, the pH of the *Stevia*-derived glycoside solution can be adjusted to a pH ranging from a pH of about 8 to a pH of about 10. In yet other embodiments, the pH of the *Stevia*-derived glycoside solution can be adjusted to pH of about 9. The pH is typically adjusted by the addition of a base. Useful bases include sodium hydroxide, potassium hydroxide, calcium oxide (lime), or calcium hydroxide.

In other embodiments, the pH of the *Stevia*-derived glycoside solution can be adjusted to a pH ranging from a pH of about 4 to a pH of about 7. In yet other embodiments, the pH of the *Stevia*-derived glycoside solution can be adjusted to a pH ranging from a pH of about 5 to a pH of about 6. In yet other embodiments, the pH of the *Stevia*-derived glycoside solution can be adjusted to a pH ranging from a pH of about 1 to a pH of about 4. In yet other embodiments, the pH of the *Stevia*-derived glycoside solution can be adjusted to a pH ranging from a pH of about 1 to a pH of about 3. In yet other embodiments, the pH of the *Stevia*-derived glycoside solution can be adjusted to pH of about 2.

Adjusting the pH can be used to alter the binding characteristics of reb-B on the adsorbent resin. For example, increasing the pH can change reb-B from strongly binding to the adsorbent resin to weakly binding to the adsorbent resin. Reducing the pH can cause reb-B to strongly bind to the resin. By adjusting the pH, the elution properties of reb-B may be altered to provide a desired enrichment profile. A summary of the binding properties of reb-B for various adsorbent resins is provided below.

| Resin | pH | reb-B |
|-------|-----|---------------|
| FPX66 | 5 | Strong Binder |
| SP710 | 9 | Weak Binder |
| SP710 | 5 | Strong Binder |
| SP70 | 9 | Weak Binder |
| SP70 | 5 | Strong Binder |

After feeding the *Stevia*-derived glycoside solution onto the adsorbent, one or more elution solvents are then fed though the adsorbent bed in order to elute one or more enriched fractions. In many embodiments, the elution solvent is formulated to cause at least a portion of the reb-B and/or reb-D that is adsorbed to be released from the adsorbent and eluted from the bed. Useful elution solvents for eluting reb-B and/or reb-D include, for example, $C_1$ to $C_3$ alcohol/water solutions (e.g., ethanol/water solutions).

The enrichment methods of the invention may be used to prepare enriched compositions comprising reb-B, reb D, or both reb-B and reb-D. In addition, the method may be used to remove reb-B and/or reb-D from reb-A compositions thereby increasing the relative purity of the reb-A. As used herein the term "enriched", means that the amount of the enriched component is increased on a dry solids basis as compared to the other glycosides present in the starting composition. For example, in the enriched composition, the amount of reb-B, reb-D, or both is increased on a dry solids basis relative to the amount that was present in the *Stevia*-derived glycoside composition that was used as the starting composition for the enrichment process. For example, in some embodiments, the purified reb-B and/or reb-D solution may comprise, on a glycoside basis, about 25 to about 90 wt % reb-A, about 10 to about 50 wt % reb-D; and 0 to about 20 wt % reb-B. In other embodiments, the purified reb-B and/or reb-D solution comprises, on a glycoside basis, about 25 to about 60 wt % reb-A, about 10 to about 50 wt % reb-D, and about 5 to about 20 wt % reb-B.

In some embodiments of the invention the enrichment process may be conducted multiple times in order to increase the final purity of the enriched composition. For example, the enriched composition from a first separation may be fed into a second chromatography bed in order to further enrich the composition in reb-B, reb-D, or mixtures thereof.

Elution solvents made up of various ratios of ethanol and water can be used to preferentially elute compositions enriched in reb-B, reb-D, or a combination of reb-B and reb-D. Applicants have surprisingly discovered that, in combination with the deliberate pH adjustment of the *Stevia*-derived glycoside solution, minor modifications in the ratio of ethanol and water in elution solvents can allow for elution of compositions enriched in reb-B, reb-D, or a combination thereof.

Reb-B and Reb-D Enrichment

In certain embodiments, reb-B and reb-D can be preferentially eluted. In these embodiments, the pH of the *Stevia*-derived glycoside solution can be a pH ranging from a pH of about 7 to a pH of about 11. In other embodiments, the pH of the *Stevia*-derived glycoside solution can be adjusted to a pH ranging from a pH of about 8 to a pH of about 11. In yet other embodiments, the pH of the *Stevia*-derived glycoside solution can be adjusted to a pH ranging from a pH of about 8 to a pH of about 10. In yet other embodiments, the pH of the *Stevia*-derived glycoside solution can be adjusted to a pH of about 9.

After deliberately adjusting the pH, reb-B and reb-D can be preferentially eluted through management of the ethanol/water ratio of the elution solvent. In an exemplary embodiment, reb-B and reb-D can be preferentially eluted using a solvent comprising about 10-50% w/w ethanol and about 50-90% w/w water. In other embodiments, the elution solvent comprises about 10-40% w/w ethanol and about 60-90% w/w water. In yet other embodiments, the elution solvent comprises about 20-35% w/w ethanol and about 65-80% w/w water. In yet other embodiments, the elution solvent comprises about 25-33% w/w ethanol and about 67-75% w/w water. Typically, the weight ratio of elution solvent to glycoside solution ranges from about 20:1 to 1:100 (parts elution solvent: parts glycoside solution), more typically ranging from about 10:1 to 1:20 (parts elution solvent: parts glycoside solution). The ratio of solvents depends strongly on the concentration of the glycosides in the glycoside containing solution.

After eluting the reb-B and reb-D enriched composition, the remaining adsorbed glycosides can be desorbed from the resin utilizing an appropriate subsequent elution solvent. The subsequent elution solvent is made up of a greater percentage of ethanol than that used to preferentially elute reb-B and reb-D. The composition eluted with this subsequent elution solvent will be enriched in reb-A. In some embodiments, this subsequent elution solvent comprises from about 36-100% w/w ethanol and 0-64% w/w water.

This subsequent elution solvent could also comprise for example, about 40-80% w/w ethanol and about 20-60% water.

Reb-D Enrichment

In other certain embodiments, reb-D can be preferentially eluted. In these embodiments, the pH of the *Stevia*-derived glycoside solution can be a pH ranging from a pH of about 4 to a pH of about 7. In other embodiments, the pH of the *Stevia*-derived glycoside solution can be adjusted to a pH ranging from a pH of about 5 to a pH of about 7. In yet other embodiments, the pH of the *Stevia*-derived glycoside solution can be adjusted to a pH ranging from a pH of about 5 to a pH of about 6. After deliberately adjusting the pH, reb-D can be preferentially eluted through management of the ethanol/water ratio of the elution solvent. In some embodiments, the elution solvent comprises about 10-40% w/w ethanol and about 60-90% w/w water. In other embodiments, the elution solvent comprises about 20-35% w/w ethanol and about 65-80% w/w water. In yet other embodiments, the elution solvent comprises about 25-33% w/w ethanol and about 67-75% w/w water. After eluting the reb-D enriched composition, the remaining adsorbed glycosides can be desorbed from the resin utilizing an appropriate subsequent elution solvent. The subsequent elution solvent is made up of a greater percentage of ethanol than that used to preferentially elute reb-D. The composition eluted with this subsequent elution solvent will be enriched in reb-A and reb-B. In some embodiments, this subsequent elution solvent comprises from about 36-100% w/w ethanol and 0-64% w/w water. This subsequent elution solvent could also comprise for example, about 40-80% w/w ethanol and about 20-60% water.

Reb-B Enrichment

In certain other embodiments, an enriched reb-B composition can be obtained. These embodiments can utilize a series of elutions. In these embodiments, the pH of the *Stevia*-derived glycoside solution can be a pH ranging from a pH of about 1 to a pH of about 4. In other embodiments, the pH of the *Stevia*-derived glycoside solution can be adjusted to a pH ranging from a pH of about 1 to a pH of about 3. In yet other embodiments, the pH of the *Stevia*-derived glycoside solution can be adjusted to a pH of about 2. In these embodiments, the pH of the *Stevia*-derived glycoside solution is selected to cause reb-B to bind very strongly to the resin.

In these embodiments, the bulk of *Stevia*-based glycosides are first eluted. In some embodiments, the elution solvent comprises about 30-70% w/w ethanol and about 30-70% w/w water. In other embodiments, the elution solvent comprises about 40-60% w/w ethanol and about 40-60% w/w water. In yet other embodiments, the elution solvent comprises about 45-55% w/w ethanol and about 45-55% w/w water. This eluted composition is enriched in reb-A and reb-D. After eluting this reb-A and reb-D enriched composition, a reb-B enriched composition can next be desorbed from the resin utilizing an appropriate subsequent elution solvent. The subsequent elution solvent is made up of a greater percentage of ethanol than that used to elute the reb-A and reb-D enriched composition. In some embodiments, the subsequent elution solvent comprises about 60-100% w/w ethanol and 0-40% w/w water. In some embodiments, the subsequent elution solvent comprises about 70-100% w/w ethanol and 0-30% w/w water. The composition eluted with this subsequent elution solvent will be enriched in and reb-B.

In embodiments of the present invention where the pH is adjusted so that reb-B is very strongly bound to the resin, utilization of multiple elutions along with the judicious management of the ethanol/water ratio in each elution can allow for compositions enriched in reb-D, reb-A, and reb-B to be eluted separately. In this embodiment, reb-D can be eluted from the column first. In some embodiments, the elution solvent to elute the reb-D enriched composition comprises about 10-40% w/w ethanol and about 60-90% w/w water. In other embodiments, the elution solvent to elute the reb-D enriched composition comprises about 20-35% w/w ethanol and about 65-80% w/w water. In yet other embodiments, the elution solvent to elute the reb-D enriched composition comprises about 25-33% w/w ethanol and about 67-75% w/w water.

After eluting the reb-D enriched composition, a reb-A enriched composition can next be eluted utilizing an appropriate subsequent elution solvent. In some embodiments, this subsequent elution solvent comprises about 40-60% w/w ethanol and about 40-60% w/w water. In other embodiments, this subsequent elution solvent comprises about 45-55% w/w ethanol and about 45-55% w/w water.

After eluting the reb-A enriched composition, a reb-B enriched composition can be eluted utilizing an appropriate further subsequent elution solvent. In some embodiments, this further subsequent elution solvent comprises about 60-100% w/w ethanol and about 0-40% w/w water. In other embodiments, this further subsequent elution solvent comprises about 65-90% w/w ethanol and about 10-35% w/w water. In yet other embodiments, this further subsequent elution solvent comprises about 70-85% w/w ethanol and about 15-30% w/w water.

The reb-D rich fraction obtained from the present invention can, on a glycoside basis, contain about 10 wt % to about 50 wt % reb-D and essentially no reb-B. The reb-B rich fraction obtained from the present invention can, on a glycoside basis, contain about 1 wt % to about 5 wt % reb-B, and essentially no reb-D.

The invention will now be described with reference to the following non-limiting examples.

EXAMPLES

The following abbreviations are used in the Examples.
RD or Reb-D: rebaudioside-D
RA or Reb-A: rebaudioside-A
Sty: stevioside
RC or Reb-C: rebaudioside-C
RF or Reb-F: rebaudioside-F
RB or Reb-B: rebaudioside-B
SB: steviolbioside
208: isomer of rebaudioside-A.
SP710: Diaion Sepabead SP710
EtOH: ethanol Example 1

*Stevia* leaf was extracted with room temperature water and an extract was obtained with 0.58% dissolved solids and a pH of 5.8. A volume of 370 ml of the steepwater was passed through a 25-ml column packed with SP710 resin held at 50° C. The column was further washed with 148 ml of water. The material passing through during loading and the initial water wash were pooled for analysis and denoted as the pass fraction. The column was sequentially eluted with 50 ml of increasing concentrations of ethanol from 20 to 60% (w/w) ethanol and 40 to 80% (w/w) water and rinsed with 35 ml of water in between each ethanol elution. Each of the water rinses and the ethanol eluents at each of the various concentrations were collected, mixed and dried for analysis. FIG. 2 is the recovery of various glycosides for each elution. Approximately 50% of the mass was not adsorbed onto the column and of the adsorbed mass, most of it was eluted from the column using a concentration of 40% (w/w) ethanol and 60% (w/w) water. Reb-D elutes off the column prior to reb-A and stevioside, with the highest concentration at about 30% ethanol.

The 30% (w/w) ethanol and 70% (w/w) water eluted fraction is enriched with reb-D as compared to the starting leaf extract.

| % glycoside | RA | Stv | RC | RB | SB | RD |
|---|---|---|---|---|---|---|
| Feed | 36.10 | 55.32 | 7.11 | 0.00 | 0.00 | 1.47 |
| 30% ethanol | 32.56 | 40.65 | 3.65 | 0.08 | 0.57 | 22.49 |

Applicants note that while this and other examples are conducted at elevated temperatures, the methods described herein can be conducted at ambient temperatures.

Example 2

*Stevia* leaf was extracted with room temperature water, treated with ferric chloride and lime, and filtered to generate a steepwater containing 0.79% solids and had a pH of 9.5. A volume of 400 ml was passed through a 25-ml SP710 column held at 50° C. at 1.6 bed volume/hour (BV/hr). The column was washed with 75 ml of water and combined with the material that passed through the column during the initial loading, and denoted as the pass fraction. Steviol glycosides were eluted off the column with 50 ml of increasing concentrations of ethanol and water from 20 to 70% (w/w) ethanol and 30 to 80% (w/w) water. 50 ml of water was used to rinse off the column in between each ethanol elution and the water rinse was combined with the ethanol fraction at each concentration before drying. FIG. 3 is the glycoside profile of the samples eluted at different ethanol concentrations. At this pH, reb-D, reb-B and steviolbioside elute off the column primarily at 30% (w/w) ethanol and 70% (w/w) water before the bulk of the reb-A and stevioside.

The 30% (w/w) ethanol and 70% (w/w) water eluted fraction is enriched with reb-D, reb-B, and steviolbioside as compared to feed.

| % glycoside | RA | Stv | RC | RD | RB | SB |
|---|---|---|---|---|---|---|
| Fe/lime | 38.9 | 52.7 | 7.4 | 0.41 | 0.32 | 0.31 |
| 30% ethanol eluent | 31.7 | 25.3 | 1.5 | 31.6 | 4.2 | 5.7 |

Example 3

A 150 ml glass column filled with SP70 resin was equilibrated with two bed volumes of a 15 wt % ethanol/85 wt % water solution. A 2 wt % solution was prepared using 15 wt % ethanol/85% water solution and a *stevia* extract lot containing 83.9% reb-A, 2.1% reb-D, 4.0% reb-B, and 1.6% Stevioside. The solution was run over the column for approximately 18.5 bed volumes, and then eluted for 2 bed volumes with a 15 wt % ethanol/85 wt % water solution, and desorbed for 3 bed volumes with 100 wt % ethanol. Loading, elution, and desorption were conducted at 55° C. at a flow rate of 2 BV/hr. Material was collected in about 50 ml samples, dried in a vacuum oven at 80° C., and analyzed by HPLC to identify the concentration of glycosides in each sample.

FIG. 4 is the concentration of glycosides eluting from the column during loading. FIG. 5 is the concentration of glycosides eluting from the column during wash with a 15% ethanol/85 wt % water solution and elution with 100% ethanol. By isolating the effluent from 10-15 BV, the material will be enriched in RD. The pooled extract would have the following composition:

| | |
|---|---|
| RebA | 79.75% |
| Stevioside | 2.14% |
| RebC | 0.37% |
| RebD | 11.00% |
| RebB | 3.52% |

Example 4

A 160 ml column filled with SP70 resin was equilibrated with water, and then loaded with 1440 ml of a water solution containing 5 g of *stevia* extract per 100 g, with pH adjusted to 2.0 by addition of citric acid. The column was loaded at 2.5 BV/hr while held at 55° C. The column was then initially washed with 1.5 BV of water, and then eluted over 4 BV with a linear gradient of ethanol, starting at 0% and ending at 100% ethanol. Finally, the column was eluted for 0.5 BV with 100% ethanol The *stevia* extract consisted of 45.6% RA, 31.8% Stev, 1.3% RF, 9.4% RC, 1.5 RD, 2.1% RB, 0.8% Dulcoside A, and 1.3% Steviolbioside. FIG. 6 is the concentration of glycosides during loading, washing, and eluting. FIG. 7 shows the mass of RA, Stev, RB and RD collected during elution. RD is primarily eluted at 30% (w/w) ethanol and 70% water; RA and Stev at 50% (w/w) ethanol and 50% water; and RB at 70% (w/w) ethanol and 30% water. Collecting the 30% ethanol eluant, 50% ethanol eluant, and 70% ethanol eluants separately allows for the separation of the extract into RD enriched, RA/Stev enriched, and RB enriched streams. Alternatively, collecting the glycosides that breakthrough the column during loading, from 3.5 to 5.5 BV, leads to a product enriched in RB and RD.

Example 5

A 120 ml column filled with SP70 resin was equilibrated with water, and then loaded with 1025 ml of a water solution containing 5 g of *stevia* extract per 100 g, with pH adjusted to 9.0 by addition of potassium hydroxide. The column was loaded at 2.5 BV/hr while held at 55° C. The column was then initially washed with 1.5 BV of water, and then eluted with 4 BV with a linear gradient of ethanol, starting at 0% and ending at 100% ethanol. Finally, the column was eluted with 4 BV of 100% ethanol. The *stevia* extract consisted of 45.6% RA, 31.8% Stev, 1.3% RF, 9.4% RC, 1.5 RD, 2.1% RB, 0.8% Dulcoside A, and 1.3% Steviolbioside. FIG. 8 is the concentration of glycosides during loading, washing, and eluting. FIG. 9 shows the mass of RA, Stev, RB and RD collected during elution. RB and RD are primarily eluted at 30% (w/w) ethanol and 70% (w/w) water; RA and Stev at 50% (w/w) ethanol and 50% (w/w) water. Collecting the 30% ethanol eluant and 50% ethanol eluant separately allows for the separation of the extract into RB/RD enriched and RA/Stev enriched streams.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. A method of preparing an enriched composition comprising rebaudioside D, the method comprising the steps of:
    (A) contacting a macroporous neutral adsorbent resin with a glycoside solution, which has a pH from about 4 to about 6 and comprises rebaudioside D and at least one other steviol glycoside, so that at least a portion of glycosides in the glycoside solution are adsorbed onto the macroporous neutral adsorbent resin; and
    (B) contacting the macroporous neutral adsorbent resin with at least one elution solvent formulated to selectively elute rebaudioside D from the adsorbent and comprising about 10-40% w/w ethanol and about 60-90% w/w water, thereby eluting a composition enriched with rebaudioside D.

2. The method according to claim 1, wherein the method further comprises, after step (B), eluting at least a portion of remaining adsorbed glycosides from the macroporous neutral adsorbent resin.

3. The method according to claim 1, wherein the at least one elution solvent comprises about 20-35% w/w ethanol and about 65-80% w/w water.

4. The method according to claim 1, wherein the at least one elution solvent comprises about 25-33% w/w ethanol and about 67-75% w/w water.

5. The method according to claim 1, wherein the macroporous neutral adsorbent resin comprises a macroporous resin of divinyl benzene.

6. An enriched composition prepared according to the method of claim 1.

* * * * *